United States Patent [19]
Bird et al.

[11] Patent Number: 4,786,495
[45] Date of Patent: Nov. 22, 1988

[54] THERAPEUTIC AGENTS

[75] Inventors: Graham Bird; Alan Smith, both of Nottingham, England

[73] Assignee: The Boots Company PLC, United Kingdom

[21] Appl. No.: 914,264

[22] Filed: Oct. 2, 1986

[30] Foreign Application Priority Data

Oct. 3, 1985 [GB] United Kingdom ............... 85/24421

[51] Int. Cl.$^4$ ...................... A61K 31/19; A61K 31/78
[52] U.S. Cl. ........................................ 424/81; 514/557
[58] Field of Search ........................... 514/557; 424/81

[56] References Cited

U.S. PATENT DOCUMENTS 3,288,824  11/1966  Mahler et al.
3,966,978  6/1976   Ellenbogen et al. ................ 424/308
4,388,307  6/1983   Cavanak.
4,473,584  9/1984   Heckler .............................. 424/308
4,477,468  10/1984  Heckler .............................. 424/308
4,514,386  4/1985   Yamahira et al. .................... 424/81
4,543,251  9/1985   Kamishita ............................ 424/81

FOREIGN PATENT DOCUMENTS 0129435  12/1984  European Pat. Off.
8604503  8/1986   PCT Int'l Appl.

OTHER PUBLICATIONS

Chem. Abstracts vol. 103, No. 20, p. 360, 166015d.
Chem. Abstracts vol. 105, p. 368, 66339k.
Chem. Abstracts vol. 105, p. 730, 158757y.
Gelucire Trade Literature "Gelucire Puts Liquid Formulations Into Hard Gelatin Capsules".
"Gelucire—Excipients for Hard Gelatin Capsules" Gelucire—BTG No. 74–1981.
The Filling of Molten and Thixotropic Formulations into Hard Gelatin Capsules. (J. Pharm. Pharmacol. 1980, 32, p. 389–393).
Diffusion and Erosion Controlled Drug Release From Lipid Matrix Formulations Incorporated into Hard Gelatin Capsules.
Derwent Abstract 80–87365 c/49.
Derwent Abstract 23213 k/10.
Derwent Abstract 86–123464/19.
Derwent Abstract 85–211497/35.
Derwent Abstract 81–87958 D/48.

Primary Examiner—Stanley J. Friedman
Attorney, Agent, or Firm—Jacobs & Jacobs

[57] ABSTRACT

A pharmaceutical composition comprising the analgesic and anti-inflammatory agent 2-(2-fluoro-4-biphenylyl)-propionic acid or a pharmaceutically acceptable salt thereof and certain esters of natural vegetable oil fatty acids, provides a rapid release of 2-(2-fluoro-4-biphenylyl)propionic acid into the body, and hence a very rapid analgesic and anti-inflammatory effect.

31 Claims, No Drawings

THERAPEUTIC AGENTS

The invention relates to therapeutic agents, and in particular to compositions comprising 2-(2-fluoro-4-biphenylyl)propionic acid.

2-(2-Fluoro-4-biphenylyl)propionic acid is a widely used non-steroidal analgesic, anti-inflammatory and antipyretic agent. In certain applications, it is desirable to provide a rapid release of the agent in order to secure a rapid effect in the body. In order to achieve this it is desired to disperse the 2-(2-fluoro-4-biphenylyl)propionic acid so that it is available for absorption as soon as possible after entering the body. However, it has been found that, in common with other acidic substances with hydrophobic properties, 2-(2-fluoro-4-biphenylyl)propionic acid is not easily dispersible in acidic media such as are found in the gastric fluids.

Many kinds of pharmaceutical excipients are known for admixture with a pharmaceutically active ingredient to provide solid, semi-solid or liquid compositions which may be presented in many different forms and which have a variety of release rates. A widely investigated class of pharmaceutical excipients known to provide advantageous wetting, dispersion and dissolution properties are polyethylene glycols which are highly hydrophilic materials and which would therefore be expected to produce a fast dispersion in aqueous media. However, it has been found that when combined with these materials, the release rate of 2-(2-fluoro-4-biphenylyl)propionic acid is not sufficiently increased to produce a rapid effect in the body. Furthermore, it would be expected that favourable release rates could be obtained where 2-(2-fluoro-4-biphenylyl)propionic acid is presented in solution, for example in a low molecular weight polyethylene glycol (e.g. polyethylene glycol having a molecular weight of 300) presented in a gelatin capsule. However, again, a sufficiently rapid release was not obtained as the combination of polyethylene glycol and 2-(2-fluoro-4-biphenylyl)propionic acid did not have satisfactory dispersion properties in acidic media.

A further well known class of pharmaceutical excipients, i.e. glyceride materials, have been found to be unsuitable for use where a rapid release of 2-(2-fluoro-4-biphenylyl)propionic acid is required, including certain mono- and diglycerides which are recommended as an acid where a rapid release of a pharmaceutically active ingredient is required. It is also known that surfactants such as Tween 80, sodium lauryl sulphate and Cremophor, which are often used to aid the dispersibility of a pharmaceutically active ingredient, when added to formulations containing 2-(2-fluoro-4-biphenylyl)propionic acid do not produce an acceptable release rate of the drug to ensure a rapid effect in the body. It is also undesirable to add large quantities of surfactant materials to formulations as they may produce undesirable side effects in the body. Thus a range of excipients with varying physical properties and hydrophilicities have been found to have little effect in presenting 2-(2-fluoro-4-biphenylyl)propionic acid so that it is available for absorption soon after it enters the body.

Unexpectedly, however, we have found that when a composition comprising 2-(2-fluoro-4-biphenylyl)propionic acid and certain esters of natural vegetable oil fatty acids is administered to the human body, the 2-(2-fluoro-4-biphenylyl)propionic acid is released from the formulation, and hence absorbed into the body, extremely rapidly. Although some of these esters are known as pharmaceutical excipients which may be selected to provide a variety of release rates, for example the Gelucire range of pharmaceutical excipients available from Gattefosse, it would not be expected, in view of the lack of success obtained with other highly hydrophilic and highly dispersible pharmaceutical excipients, that these esters of natural vegetable oil fatty acids would produce such an accelerated rate of release and absorption into the body. We have observed that 2-(2-fluoro-4-biphenylyl)propionic acid in the combination is absorbed by the body at a substantially faster rate than when it is provided in the more normal solid dosage form of a tablet. This result is surprising, as the rate of absorption of 2-(2-fluoro-4-biphenylyl)propionic acid from a solid dosage form would not normally be expected to be faster than that from a tablet. In fact the 2-(2-fluoro-4-biphenylyl)propionic acid is absorbed by the body from this composition at a rate comparable to that when the active ingredient is provided in the form of a liquid formulation.

Accordingly, the invention provides a pharmaceutical composition comprising 2-(2-fluoro-4-biphenylyl)propionic acid or a pharmaceutically acceptable salt thereof and an excipient which comprises one or more polyol esters and glycerides of natural vegetable oil fatty acids (hereinafter referred to as the fatty acid esters excipient) said excipient having a melting point less than 55° C. and an HLB value of at least 10.

A composition according to the invention has particular advantages in solid formulations, in particular solid formulations contained within hard gelatin capsules.

We have found that when compared to normal solid dosage forms containing 2-(2-fluoro-4-biphenylyl)propionic acid, substantially faster in vitro dispersion and dissolution of the propionic acid is achieved from a composition of this invention. Furthermore, we have also found that the solubility of 2-(2-fluoro-4-biphenylyl)propionic acid released from a composition according to the invention is markedly increased, particularly in acidic media such as would be found in the stomach. A fast dispersion will ensure that 2-(2-fluoro-4-biphenylyl)propionic acid is rapidly made available for absorption into the body. A high dissolution rate combined with increased solubility will further increase the rate of absorption of the drug by the body and will lead to a reduction in the time in which the drug takes effect in the body as compared to normal solid unit dosage forms. Advantageous dispersion, dissolution and solubility properties are obtained at all values of the pH range to be found in the body. However this effect is significant in acidic media for example at pH 4, but is particularly marked at pH 2.2 which is similar to that found in the gastric fluids.

It is desired that the fatty acid esters excipient has a high HLB value, i.e. above a value of 10. Preferred HLB values are at least 12, especially 12 to 14. The HLB value is the hydrophilic-lipophilic balance which is defined as the ratio of the respective hydrophilic and hydrophobic portions of an amphiphatic molecule. The fatty acid esters excipient requires a high HLB value to ensure that the excipient disperses rapidly in the gastric fluids.

The fatty acid esters excipient used in this invention has a melting point less than 55° C., conveniently in the range of 18°–55° C., preferably 30°–50° C., most preferably 35°–45° C. As a result of the addition of the 2-(2-fluoro-4-biphenylyl)propionic acid to the fatty acid esters excipient the melting point of the composition may differ from that of the fatty acid esters excipient. An advantageous melting point of the combination of 2-(2-fluoro-4-biphenylyl)propionic acid and fatty acid esters excipient is less than 50° C., particularly in the range of 33°-46° C. It is especially desired that when combined with the 2-(2-fluoro-4-biphenylyl)propionic acid the combination melts at a temperature of between 36° and 42° C., i.e. around that of body temperature. A melting temperature of around 37° C. allows the composition of the invention to be melted and dispersed substantially as soon as it enters the body for example by release from a gelatin capsule; and hence allows the active ingredient to be released into the body substantially immediately. In addition, a melting point of approximately 37° C. for the composition is sufficiently high that the composition will not be caused to melt at normal storage temperatures which would be detrimental to storage stability. The melting points of compositions according to the invention have been measured by differential scanning calorimetry at a heating rate of 10° C. per minute in a nitrogen atmosphere. It will be appreciated by those skilled in the art that the melting range can be distributed fairly widely about the melting point.

The fatty acid esters excipients found to satisfy the above-mentioned properties include those having the following melting point and HLB values: mp 35° C./HLB 10; mp 42° C./HLB 12; mp 50° C./HLB 13; and preferably mp 44° C./HLB 14. The most advantageous fatty acid esters excipients are those having a melting point in the range 37°-50° C. and a HLB value of 11 to 14, especially those having a melting point from 40°-44° C. and HLB value from 12 to 14, and in particular melting point 40°-44° C. and HLB value about 14.

Alternatively, two or more excipients may be combined to provide a combination fatty acid excipient having a melting point and HLB value in the range as hereinabove described.

The fatty acid esters excipients for use in this invention may be prepared by esterifying a natural vegetable oil with glycerol and a polyol. Advantageously, a homogeneous mixture containing triglycerides, diglycerides, monoglycerides, dipolyglycides and monopolyglycides is formed. Preferably the fatty acid component contains 8–22 carbon atoms, especially 10–18 carbon atoms. Examples of natural vegetable oils employed include palmkernel oil and palm oil. The polyol suitably has a molecular weight in the range 300–1500 and preferably comprises polyethylene glycol, although other polyols may be employed e.g. polyglycerols, sorbitol etc. Further details are given in Technical Bulletin No. 74, 1981 (Gattefosse Co. St. Priest, France) under the term Gelucire. (See Chem. Abs., Vol. 97, No. 188206).

When 2-(2-fluoro-4-biphenylyl)propionic acid or its pharmaceutically acceptable salts is admixed with the fatty acid esters excipient a dispersion or solution of the pharmaceutically active ingredient, 2-(2-fluoro-4-biphenylyl)propionic acid, in the excipient is formed. The solubility of 2-(2-fluoro-4-biphenylyl)propionic acid or its pharmaceutically acceptable salt has an influence on the amount of active ingredient in the composition. A greater solubility will allow a greater proportion of active ingredient to be included in the composition. It is not necessary that the active ingredient is soluble in the fatty acid esters excipient, but care should be taken to ensure that a homogeneous dispersion is formed in order to obtain the most advantageous results. Suitably the 2-(2-fluoro-4-biphenylyl)propionic acid is present to an extent of up to 40% by weight of the composition. Above this value the rate of dissolution of the composition in the gastric fluids is impaired. Desirably the 2-(2-fluoro-4-biphenylyl)propionic acid is used in the range of 5–35% by weight of the composition, advantageously 10–25% by weight of the composition. The amount of 2-(2-fluoro-4-biphenylyl)propionic acid in the composition may affect the melting point of the composition as in some cases a eutectic mixture may be formed. It has generally been found that the dissolution properties of a composition according to the invention are enhanced as the amount of 2-(2-fluoro-4-biphenylyl)propionic acid is decreased. However, in a preferred composition according to the invention comprising flurbiprofen and a fatty acid esters excipient having a m.pt. of 44° C. and a HLB value of 14, when the flurbiprofen comprises less than about 14% by weight of the composition the melting point of the composition is not reduced to the preferred temperature of 37° C. This may lead to a slower rate of release of the flurbiprofen. Generally, we prefer to use not less than 5% 2-(2-fluoro-4-biphenylyl)propionic acid by weight of the composition. In a preferred composition 2-(2-fluoro-4-biphenylyl)propionic acid comprises 14–20% by weight of the total composition. Where a pharmaceutically acceptable salt of 2-(2-fluoro-4-biphenylyl)propionic acid is employed, the quantity of salt contained within the composition may be greater than when 2-(2-fluoro-4-biphenylyl)propionic acid is used in order to provide an equivalent level of active ingredient.

The compound 2-(2-fluoro-4-biphenylyl)propionic acid has a chiral centre and thus exists in two enantiomeric forms. The present invention includes both enantiomers and mixtures thereof. In particular the invention relates to the racemate i.e. flurbiprofen, and to the (+)isomer, i.e. esflurbiprofen and to their pharmaceutically acceptable salts.

Suitable pharmaceutically acceptable salts of 2-(2-fluoro-4-biphenylyl)propionic acid include sodium potassium, meglumine, arginine, choline and lysine salts. Particular advantages have been found by the use of the sodium salt of 2-(2-fluoro-4-biphenylyl)propionic acid especially in respect of improved stability.

Further excipients may be added to the composition to modify the release rate of 2-(2-fluoro-4-biphenylyl)propionic acid from the formulation into the body.

Excipients may be added to modify the melting point and hydrophilicity of a composition according to the invention, for example glycerol, vegetable and mineral oils, water or polyols, in particular polyethylene glycol. The quantity of excipient employed depends on the characteristics required and the nature of the excipient. Preferably the level of these excipients is from 5–50% by weight, especially from 5–20% by weight.

Excipients may also be added to further enhance the wetting properties and solubility of the 2-(2-fluoro-4-biphenylyl)propionic acid in the gastro-intestinal fluids, for example surface active agents e.g. Tween (trade mark), Cremophor (trade mark), sodium lauryl sulphate, Brij (trade mark) and Pluronic (trade mark) and pH modifying agents including sodium carbonate, buffers e.g. sodium citrate, and bases e.g. meglumine or salts thereof.

There may also be incorporated into the compositions of the present invention additional edible non-toxic ingredients recognised in the art of pharmaceutical formulation such as binders, for example pregelled starches, microcrystalline cellulose, gelatin, gums; soluble diluents, for example lactose, sodium chloride, dextrins, sorbitol; lubricants for example magnesium stearate; flow aids such as talc; and othe oils, fats and waxes.

Also suitable pharmaceutically acceptable excipients which produce accelerated rates of dispersion and dissolution are generally disintegrants such as the following, or mixtures thereof: vegetable starches and starch derivatives; cellulose, cellulose derivatives and modified cellulose derivatives, sodium croscarmellose (Acidsol—trade mark), sodium starch glycollate (Explotab—trade mark), cross-linked polyvinylpyrrolidones such as Kollidon XL (trade mark) and Crosprovidone (trade mark).

For a more rapid release of 2-(2-fluoro-4-biphenylyl)-propionic acid from the composition, an excipient or mixture of excipients may be employed which contain at least one accelerant as exemplified above. For the more potent disintegrants, such as sodium croscarmellose, and sodium starch glycollate, a low level of excipient may be used for example from 0.1 to 10% especially from 2–5% by weight of the composition. For less potent disintegrants such as starches, higher levels should be used, for example from 2.5–50%, preferably at least 5% and especially from 10–20% by weight.

Preferably the unit dosage is provided in the form of a solution or dispersion of 2-(2-fluoro-4-biphenylyl)propionic acid in the fatty acid esters excipient contained within a capsule, most desirably a hard gelatin capsule. It is desired that the capsule dissolves quickly in the gastric fluids to allow the quick release of the drug from the composition. Alternatively, the dosage form may also be presented as a soft gelatin capsule. Optionally it may also be presented in the form of tablets, lozenges, pastilles, suppositories and implants. Generally, though not exclusively, these compositions may be formed by allowing the molten mixture of 2-(2-fluoro-4-biphenylyl)propionic acid in the fatty acid esters excipient to solidify in a shaped mould. When a composition according to the invention is provided for administration in a capsule, the capsule may be of any size convenient for oral administration to humans. Suitable sizes include sizes 00, 0, 1, 2, 3 and 4. Each unit dose composition suitably contains 25 to 200 mg of 2-(2-fluoro-4-biphenylyl)propionic acid, preferably 25–100 mg.

2-(2-Fluoro-4-biphenylyl)propionic acid is a nonsteroidal analgesic, anti-inflammatory and antipyretic agent. Compositions according to the invention are therefore suitable for analgesic, anti-inflammatory and antipyretic use.

In the preparation of the unit dosage form the solid fatty acid esters excipient is heated so that it is melted and the 2-(2-fluoro-4-biphenylyl)propionic acid is added in the form of a powder. The two components plus any other optional excipients are stirred to form a homogeneous dispersion which is then allowed to solidify. Where the composition is presented in the form of a capsule, for example a hard gelatin capsule, the molten dispersion of 2-(2-fluoro-4-biphenylyl)propionic acid in fatty acid esters excipient is dispensed into the capsule and allowed to solidify. Where two or more fatty acid esters excipients are used, they may be combined to form a homogenous molten solution and 2-(2-fluoro-4-biphenylyl)propionic acid then added to the molten mixture. Where other excipients are added appropriate modifications may be made to the process. For example, where a further liquid excipient is employed, e.g. polyethylene glycol or glycerol, it is advantageous to add it to the molten fatty acid esters excipient before the addition of 2-(2-fluoro-4-biphenylyl)propionic acid. Where it is desired to add a further solid excipient in the form of a powder, advantageously it is mixed with the fatty acid esters excipient to form a homogenous molten dispersion before the addition of 2-(2-fluoro-4-biphenylyl)propionic acid. Alternatively, the further powder excipient may be combined with 2-(2-fluoro-4-biphenylyl)propionic acid, and the resulting powder composition added to the molten fatty acid esters excipient, which then is mixed to form a homogeneous molten dispersion. If desired a solution or suspension of 2-(2-fluoro-4-biphenylyl)propionic acid may be combined with the molten fatty acid esters excipient.

The invention is illustrated by the following non-limitative Examples.

EXAMPLE 1

A formulation containing per size 1 capsule
flurbiprofen 50 mg
Gelucire 44/14 300 mg
was prepared by warming Gelucire 44/14 to 70° C. and adding flurbiprofen with stirring to form a homogeneous molten solution. The solution was transferred to a heated reservoir feeding a volumetric pump and capsules were filled via the pump.

(Gelucire is the Trade Name for a fatty acid esters excipient as hereinbefore defined, available from the Gattefosse Co., Saint-Priest, France.)

EXAMPLE 2

A formulation containing per size 0 capsule
flurbiprofen 50 mg
Gelucire 44/14 350 mg
was prepared by warming Gelucire 44/14 to 60° C. and adding flurbiprofen with stirring to form a homogeneous molten solution. The solution was filled volumetrically by pipette into a hard gelatin capsule.

EXAMPLE 3

A formulation containing per size 1 capsule
flurbiprofen 75 mg
Gelucire 44/14 300 mg
was prepared by warming Gelucire 44/14 to 75° C. and adding flurbiprofen with stirring to form a homogeneous molten solution. The solution was filled volumetrically by pipette into a hard gelatin capsule.

In Examples 1–3 it is also possible to substitute Gelucire 42/12, 35/10 or 50/13 or mixture thereof which provide the melting point/HLB value as required by this invention.

EXAMPLE 4

A formulation containing per size 1 capsule
flurbiprofen 50 mg
Gelucire 35/10 30 mg
Gelucire 44/14 270 mg
was prepared by warming Gelucire 44/14 and Gelucire 35/10 to 45° C. and adding flurbiprofen with stirring to form a homogeneous molten solution. The solution was filled gravimetrically by pipette into a hard gelatin capsule.

EXAMPLE 5

A formulation containing per size 1 capsule
flurbiprofen 100 mg
Sodium lauryl sulphate 20 mg
Gelucire 44/14 300 mg was prepared by intimately mixing sodium lauryl sulphate and flurbiprofen in a pestle and mortar. The mixture was added to molten Gelucire 44/14 at 60° C. before being filled by pipette into a hard gelatin capsule.

EXAMPLE 6

A formulation containing per size 1 capsule
flurbiprofen (as sodium salt) 50 mg
Gelucire 44/14 300 mg
was prepared by warming Gelucire 44/14 to 60° C. and adding the sodium salt of flurbiprofen with stirring to form a homogeneous molten dispersion. The liquid was transferred to a heated reservoir feeding a volumetric pump and capsules were filled via the pump.

EXAMPLE 7

A similar formulation was made in the same way as example 6 using 50 mg of flurbiprofen (as the sodium salt) and 250 mg Gelucire 44/14.

EXAMPLE 8

A similar formulation in a size 0 capsule was made in the same way as example 6 using 50 mg of flurbiprofen (as the sodium salt) and 350 mg Gelucire 44/14.

EXAMPLE 9

A formulation containing per size 1 capsule
(+)-flurbiprofen 50 mg
Gelucire 44/14 300 mg
was prepared in the same manner as described in Example 6.

EXAMPLE 10

A formulation containing per size 1 capsule
flurbiprofen (as sodium salt) 50 mg
Gelucire 42/12 300 mg was prepared in the same manner as described in Example 6.

EXAMPLE 11

A formulation containing per size 1 capsule
flurbiprofen (as sodium salt) 50 mg
Gelucire 44/14 270 mg
Glycerol 30 mg
was prepared by warming Gelucire 44/14 to 60° C. and adding the glycerol with stirring to the molten solution. The sodium salt of flurbiprofen was then added to the molten solution with stirring to form a homogenous molten dispersion. This was filled volumetrically by pipette into a hard gelatin capsule.

EXAMPLE 12

A formulation containing per size 1 capsule
flurbiprofen (as sodium salt) 50 mg
Gelucire 44/14 270 mg
Polyethylene glycol 200 30 mg
was prepared in the same manner as described in Example 11.

EXAMPLE 13

In vitro dissolution studies

These studies were performed at 37° C. using 900 ml medium buffered at pH 4 or pH 2.2 and stirred at 50 rpm (paddles). The dissolution of 2-(2-fluoro-4-biphenylyl)-propionic acid was monitored continuously by ultraviolet spectrophotometry and the amount dissolved was plotted against time in minutes over a period of one hour.

The initial rate of dissolution (µg/ml/min) was determined graphically from each dissolution profile, allowance being made from the short lag-time incurred through rupture of the capsule shell.

The dissolution characteristics are further described by the concentration of 2-(2-fluoro-4-biphenylyl)propionic acid after 20 minutes ($C_{20}$) and the concentration attained at one hour ($C_f$) from which one can identify very slow dissolution rates (i.e. $C_f < 10$ at pH 4) or systems in which 2-(2-fluoro-4-biphenylyl)propionic acid solubility is markedly increased (i.e. $C_f > 30$ at pH 4).

The initial dissolution rates, concentration of 2-(2-fluoro-4-biphenylyl)propionic acid after 20 minutes ($C_{20}$) and the one hour ($C_f$) for compositions comprising 2-(2-fluoro-4-biphenylyl)propionic acid and various excipients from the Gelucire range are shown in Tables 1, 2 and 3 below. Comparative examples using excipients known in the art are shown in Tables 4 and 5. 2-(2-Fluoro-4-biphenylyl)propionic acid is in the form of flurbiprofen except where indicated otherwise.

TABLE 1

Dissolution Characteristics of compositions comprising 2-(2-fluoro-4-biphenylyl)propionic acid and a Fatty Acid Esters Excipient at pH 4

| Fatty acid esters excipient | % Flurbiprofen | Drug content (mg) | Initial Rate ($\mu gml^{-1} min^{-1}$) | $C_{20}$ ($\mu gml^{-1}$) | $C_f$ ($\mu gml^{-1}$) |
|---|---|---|---|---|---|
| Gelucire 44/14 | 12.5 | 50 | 6.0 | 29 | 45 |
| Gelucire 50/13 | 12.5 | 50 | 0.1 | 5 | 10 |
| Gelucire 44/14 | 14.3 | 50 | 6.0 | 29 | 42 |
| Gelucire 44/14 | 14.3[1] | 50 | 6.0 | 29 | 45 |
| Gelucire 44/14 | 14.3[2] | 50 | 1.0 | 17 | 37 |
| Gelucire 44/14 + 5% sodium lauryl sulphate | 14.3 | 50 | 4.5 | 45 | 45 |
| Gelucire 44/14 + 5% Cremophor RH40 | 14.3 | 50 | 4.5 | 48 | 48 |
| Gelucire 44/14 + 10% Aerosil[3] | 14.3 | 50 | 1.5 | 14 | 20 |
| Gelucire 42/12 | 14.3[2] | 50 | 0.3 | 7 | 20 |
| Gelucire 42/12 + 30% glycerol | 14.3 | 50 | 0.7 | 14 | 18 |
| Gelucire 35/10 | 14.3 | 50 | 0.1 | 0.6 | 3 |
| 90% Gelucire 44/14 + 10% Gelucire 35/10 | 14.3 | 50 | 2.0 | 23.5 | 38 |
| 90% Gelucire 44/14 + 10% | 14.3 | 50 | 1.0 | 10.8 | 30 |

TABLE 1-continued

Dissolution Characteristics of compositions comprising 2-(2-fluoro-4-biphenylyl)propionic acid and a Fatty Acid Esters Excipient at pH 4

| Fatty acid esters excipient | % Flurbiprofen | Drug content (mg) | Initial Rate ($\mu gml^{-1} min^{-1}$) | $C_{20}$ ($\mu gml^{-1}$) | $C_f$ ($\mu gml^{-1}$) |
|---|---|---|---|---|---|
| Gelucire 50/13 |  |  |  |  |  |
| 50% Gelucire 44/14 + 50% Gelucire 35/10 | 14.3 | 50 | 0.5 | 3.0 | 13 |
| 50% Gelucire 44/14 + 50% Gelucire 50/13 | 14.3 | 50 | 0.3 | 2.5 | 10 |
| Gelucire 44/14 | 25.0[4] | 100 | 6 | 15 | 75 |
| Gelucire 50/13 | 25.0[4] | 100 | 0.5 | 10 | 20 |
| Gelucire 35/10 | 25.0[4] | 100 | 4.0 | 20 | 40 |

Notes:
[1] 2-(2-fluoro-4-biphenylyl)propionic acid is in the form of esflurbiprofen
[2] 2-(2-fluoro-4-biphenylyl)propionic acid is in the form of its sodium salt
[3] Aerosil is colloidal silica available from Degussa
[4] Unbuffered media

TABLE 2

Dissolution Characteristics of compositions comprising 2-(2-fluoro-4-biphenylyl)propionic acid and a Fatty Acid Esters Excipient at pH 2.2

| Fatty acid esters excipient | % Flurbiprofen | Drug content (mg) | Initial Rate ($\mu gml^{-1} min^{-1}$) | $C_{20}$ ($\mu gml^{-1}$) | $C_f$ ($\mu gml^{-1}$) |
|---|---|---|---|---|---|
| Gelucire 44/14 | 14.3 | 50 | 2.5 | 21 | 26 |
| Gelucire 44/14 + 10% sodium bicarbonate | 14.3 | 50 | 2.0 | 32 | 38 |
| Gelucire 44/14 | 14.3[1] | 50 | 1.5 | 20 | 40 |
| Gelucire 42/12 + 30% glycerol | 14.3 | 50 | 2.0 | 14 | 15 |
| Gelucire 50/13 + 30% glycerol | 14.3 | 50 | 0.2 | 2 | 6 |
| Gelucire 50/13 + 40% PEG 300[2] + 10% Tween 80 | 14.3 | 50 | 0.3 | 3.2 | 9 |
| Gelucire 50/13 + 40% PEG 300[2] + 10% Tween 80 | 14.3[1] | 50 | 0.2 | 1.0 | 5 |
| Gelucire 35/10 + 40% PEG 300[2] + 10% Tween 80 | 14.3 | 50 | 0.3 | 5 | 14 |
| Gelucire 35/10 + 40% PEG 300[2] + 10% Tween 80 | 14.3[1] | 50 | 0.8 | 18 | 26 |

Notes:
[1] Sodium salt of 2-(2-fluoro-4-biphenylyl)propionic acid
[2] Liquid polyethylene glycol having a molecular weight of 300

TABLE 3

Dissolution of Flurbiprofen Formulations based upon Gelucire 44/14 at pH 4

| Drug content (mg) | % Flurbiprofen | Capsule size | Initial rate ($\mu g/ml/min$) | $C_{20}$ ($\mu g/ml$) | $C_f$ ($ug/ml$) |
|---|---|---|---|---|---|
| 50 | 12.5 | 0 | 6.0 | 29 | 45 |
|  | 12.5 | 1 | 6.0 | 29 | 45 |
|  | 13.3 | 1 | 6.0 | 29 | 45 |
|  | 14.3 | 1 | 6.0 | 29 | 42 |
|  | 13.4[1] | 1 | 1.2 | 22 | 37 |
|  | 15.3[1] | 1 | 1.0 | 17 | 37 |
|  | 17.7[1] | 1 | 0.9 | 16 | 36 |
| 75 | 12.5 | 0 | 4.0 | 40 | 63 |
|  | 15.0 | 0 | 2.5 | 40 | 62 |
|  | 20.0 | 1 | 2.5 | 35 | 59 |
|  | 25.0 | 1 | 2.5 | 30 | 50 |
|  | 30.0 | 1 | 0.9 | 10 | 23 |
|  | 40.0 | 1 | 0.3 | 1 | 4 |
|  | 50.0 | 1 | 0.2 | 1 | 4 |

Notes:
[1] sodium salt of 2-(2-fluoro-4-biphenylyl)propionic acid

The initial rate measures the rate at which 2-(2-fluoro-4-biphenylyl)propionic acid or its pharmaceutically active salts was released into an aqueous vehicle and was indicated of the rate at which the 2-(2-fluoro-4-biphenylyl)propionic acid was released into the gastric fluids. $C_{20}$ shows the high rate at which dissolution occurred and provides further evidence of the enhanced release rate into solution. $C_f$ is indicative of the rate at which 2-(2-fluoro-4-biphenylyl)propionic acid or its pharmaceutically acceptable salts was dissolved or may be used to identify excipients which considerably enhance the solubility. The values shown in Tables 1, 2 and 3 may be compared with comparative examples in Tables 4 and 5 below. The rate of dissolution and the solubility of 2-(2-fluoro-4-biphenylyl)propionic acid or its pharmaceutically acceptable salts in a composition according to the invention can be seen to be improved over known compositions.

TABLE 4

Dissolution Characteristics of compositions containing 50 mg Flurbiprofen and other Comparative Excipients at pH 4

| Comparative Excipient | Flurbiprofen % | Initial Rate ($\mu$gml$^{-1}$min$^{-1}$) | $C_{20}$ ($\mu$gml$^{-1}$) | $C_f$ ($\mu$gml$^{-1}$) |
|---|---|---|---|---|
| Tablet | 25 | 0.2 | 3 | 5 |
| Lactose[1][2] | 12.5 | 1.3 | 20 | 26 |
| PEG 300[3] + 3% Carbopol[2][4] | 12.5 | 2.0 | 15 | 18 |
| PEG 6000[2][5][6] | 12.5 | 1.2 | 16 | 18 |
| PEG 6000[5][7] | 12.5 | 0.5 | 7 | 11 |
| PEG 6000[1][5] + 5% Tween 80 | 14.3 | 0.6 | 7 | 10 |
| Imwitor (A)[8] | 14.3 | 0.2 | 2.5 | 3 |
| Imwitor (B)[11] | 14.3 | 0.8 | 8 | 11 |

Notes for Table 4:
[1] Intimate mixture loose filled into gelatin capsules;
[2] Stirring paddles operating at 90 rpm;
[3] Liquid polyethylene glycol having an average molecular weight of 300;
[4] Carbopol is a carboxy vinyl polymer available from B F Goodrich;
[5] Polyethylene glycol having an average molecular weight of 6000;
[6] Melted, ground and loose filled into capsules;
[7] Melt filled into gelatin capsule;
[8] Imwitor (A) is 78.6% Imwitor 742[9] + 21.4% Imwitor 191[10];
[9] Medium chain partial glycerides comprising mono, di, triglycerides and free glycerin available Dynamit Nobel;
[10] Monoglyceride available from Dynamit Nobel;
[11] Imwitor (B) is Imwitor (A) + 30% glycerin + 1% sodium lauryl sulphate.

TABLE 5

Dissolution Characteristics of compositions containing 50 mg Flurbiprofen and other Comparative Excipients at pH 2.2

| Comparative Excipient | Flurbiprofen % | Initial Rate ($\mu$gml$^{-1}$min$^{-1}$) | $C_{20}$ ($\mu$gml$^{-1}$) | $C_f$ ($\mu$gml$^{-1}$) |
|---|---|---|---|---|
| Lactose[5] | 14.3 | 0.22 | 5.7 | 10 |
| PEG 6000[1][4] | 14.3 | 0.3 | 4.5 | 7 |
| Imwitor (A)[2] | 14.3 | 0.01 | <0.3 | 0.5 |
| Miglyol[3] | 14.3 | 0.03 | 0.6 | 2.5 |

Notes:
[1] Polyethylene glycol having a molecular weight of 6000
[2] See Table 4 above
[3] A triglyceride material available from Dynamit Nobel
[4] Melt filled into gelatin capsule
[5] Intimate mixture of flurbiprofen and lactose loose filled into gelatin capsules

EXAMPLE 14

A bioavailability study on 50 mg flurbiprofen in each of the Fast Release capsule prepared according to Example 1, a tablet and a syrup was carried out in humans by the following method. Following an overnight fast the volunteers received one of the formulations with 100 ml water according to a pre-determined randomisation schedule. Blood samples were taken before administration of the dose and after 0.25, 0.5, 0.75, 1, 1.25, 1.5, 1.75, 2, 2.5, 3, 4, 6 and 8 hours. Plasma was separated from the blood samples after centrifugation and stored frozen until assayed for flurbiprofen by an HPLC method. A hot beverage was provided after the 2 hour blood sample and lunch after the 4 hour blood samples.

From the table below it can be seen that as expected the syrup formulation was very rapidly absorbed, achieving peak concentrations sooner than the capsule or tablet formulations since no disintegration process was involved. The plasma profiles of the fast release capsule formulation show a distinct time lag while the contents of the capsule dispersed, but once this occurs absorption appeared to be as rapid as from the syrup. The film-coated tablet disintegrated more slowly, resulting in a slower rate of absorption of the flurbiprofen.

From Table 6 it can be seen that the in vivo performance of the new capsule formulation confirms the rapid in vitro release characteristics.

TABLE 6

Plasma Concentrations ($\mu$g ml$^{-1}$) of Flurbiprofen in volunteers following 50 mg Flurbiprofen in the Fast Release Capsule, Tablet or Syrup

| Time | Fast Release Capsule | Tablet | Syrup |
|---|---|---|---|
| 0.00 | N.D | N.D | N.D. |
| 0.25 | N.D | 0.8 | 6.9 |
| 0.5 | 6.3 | 1.6 | 7.9 |
| 0.75 | 8.4 | 2.3 | 7.4 |
| 1.0 | 7.8 | 3.4 | 6.8 |
| 1.25 | 7.5 | 5.0 | 6.6 |
| 1.5 | 7.2 | 6.3 | 6.1 |
| 1.75 | 6.5 | 7.1 | 5.7 |
| 2.0 | 6.0 | 6.9 | 5.3 |
| 2.5 | 5.0 | 6.2 | 4.3 |
| 3.0 | 4.2 | 4.5 | 3.6 |
| 4.0 | 2.9 | 3.2 | 2.7 |
| 6.0 | 2.0 | 1.9 | 1.7 |
| 8.0 | 1.3 | 1.1 | 1.2 |

N.D = none detected (i.e <0.5 $\mu$g/ml)

We claim:

1. A method of treating inflammation in humans and animals which comprises orally administering to a human or animal in need thereof an anti-inflammatory effective amount of 2-(2-fluoro-4-biphenylyl)propionic acid or a pharmaceutically acceptable salt thereof and an amount of excipient sufficient to produce a rapid release of the active agent into the human or animal, said excipient being one suitable for formulating solid orally administerable pharmaceutical compositions and further being a fatty acid ester which comprises one or more polyol esters and glycerides of natural vegetable oil fatty acids, said excipient having a melting point in the range of 30°-50° C. and an HLB value of at least 10.

2. A method according to claim 6 wherein the fatty acid esters have HLB value of at least 12.

3. A method according to claim 2 wherein the fatty acid esters have a HLB value of at least 14.

4. A method according to claim 3 wherein the fatty acid esters have a melting point in the range of 33°-46° C.

5. A method according to claim 4 wherein the natural vegetable oil fatty acids have 8 to 22 carbon atoms.

6. A method according to claim 1 wherein the polyol esters comprise esters of polyethylene glycol.

7. A method according to claim 1 wherein 2-(2-fluoro-4-biphenylyl)propionic acid comprises up to 40% by weight of the 2-(2-fluoro-4-biphenylyl)propionic acid and excipient.

8. A method according to claim 1 wherein 2-(2-fluoro-4-biphenylyl)propionic acid is in the form of flurbiprofen.

9. A method according to claim 1 wherein the 2-(2-fluoro-4-biphenylyl)propionic acid is in the form of the sodium salt.

10. A method according to claim 1 in which a hard gelatin capsule comprising said 2-(2-fluoro-4-biphenylyl)propionic acid and said excipient is administered.

11. A method of effecting analgesia in humans and animals which comprises orally administering to a human or animal in need thereof an analgesically effective amount of 2-(2-fluoro-4-biphenylyl)propionic acid or a pharmaceutically acceptable salt thereof and an amount of excipient sufficient to produce a rapid release of the active agent into the human or animal, said excipient being one suitable for formulating solid orally administerable pharmaceutical compositions and further being a fatty acid ester which comprises one or more polyol esters and glycerides of natural vegetable oil fatty acids, said excipient having a melting point in the range of 30°–50° C. and an HLB value of at least 10.

12. A method according to claim 11 wherein the fatty acid esters have a HLB value of at least 12.

13. A method according to claim 12 wherein the fatty acid esters have a HLB value of at least 14.

14. A method according to claim 13 wherein the fatty acid esters have a melting point in the range of 33°–46° C.

15. A method according to claim 14 wherein the natural vegetable oil fatty acids have 8 to 22 carbon atoms.

16. A method according to claim 11 wherein the polyol esters comprise esters of polyethylene glycol.

17. A method according to claim 11 wherein 2-(2-fluoro-4-biphenylyl)propionic acid comprises up to 40% by weight of the 2-(2-fluoro-4-biphenylyl)propionic acid and excipient.

18. A method according to claim 11 wherein 2-(2-fluoro-4-biphenylyl)propionic acid is in the form of flurbiprofen.

19. A method according to claim 11 wherein the 2-(2-fluoro-4-biphenylyl)propionic acid is in the form of the sodium salt.

20. A method according to claim 11 in which a hard gelatin capsule comprising said 2-(2-fluoro-4-biphenylyl)propionic acid and said excipient is administered.

21. A solid pharmaceutical composition in oral administration form useful for treating pain, inflammation and fever in humans and animals, which comprises 2-(2-fluoro-4-biphenylyl)propionic acid or a pharmaceutically acceptable salt thereof and an amount of excipient sufficient to produce a rapid release of the active agent into the human or animal, said excipient being one suitable for formulating solid orally administerable pharmaceutical compositions and further being a fatty acid ester which comprises one or more polyol esters and glycerides of natural vegetable oil fatty acids, said excipient having a melting point in the range of 30°–50° C. and an HLB value of at least 10.

22. A pharmaceutical composition according to claim 21 wherein the fatty acid esters has a HLB value of at least 12.

23. A pharmaceutical composition according to claim 22 wherein the fatty acid esters have a HLB value of at least 14.

24. A pharmaceutical composition according to claim 23 wherein the fatty acid esters have a melting point in the range of 33°–46° C.

25. A pharmaceutical composition according to claim 24 wherein the natural vegetable oil fatty acids have 8 to 22 carbon atoms.

26. A pharmaceutical composition according to claim 21 wherein the polyol esters comprise esters of polyethylene glycol.

27. A pharmaceutical composition according to claim 21 wherein 2-(2-fluoro-4-biphenylyl)propionic acid comprises up to 40% by weight of the composition.

28. A pharmaceutical composition according to claim 21 wherein 2-(2-fluoro-4-biphenylyl)propionic acid is in the form of flurbiprofen.

29. A pharmaceutical composition according to claim 21 wherein the 2-(2-fluoro-4-biphenylyl)propionic acid is in the form of the sodium salt.

30. A pharmaceutical composition according to claim 21 in the form of a hard gelatin capsule.

31. A process for making a pharmaceutical composition of claim 21 in which 2-(2-fluoro-4-biphenylyl)propionic acid is added to the fatty acid esters excipient in molten form with stirring to form a homogeneous solution or dispersion and allowing the composition to solidify.

* * * * *